US008192933B2

(12) United States Patent
Braastad et al.

(10) Patent No.: US 8,192,933 B2
(45) Date of Patent: *Jun. 5, 2012

(54) METHODS OF DETECTING MUTATIONS ASSOCIATED WITH ATAXIA-OCULAR APRAXIA 2 (AOA2)

(75) Inventors: Corey D. Braastad, Southampton, MA (US); Narasimhan Nagan, South Grafton, MA (US); Jeffrey G. Jones, Wilbraham, MA (US); William K. Seltzer, Holden, MA (US); Susan Allen, Worcester, MA (US); Sat Dev Batish, New York, NY (US); Hui Zhu, Belmont, MA (US)

(73) Assignee: Athena Diagnostics, Inc., Worcester, MA (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/722,078

(22) Filed: Mar. 11, 2010

(65) Prior Publication Data
US 2010/0167305 A1 Jul. 1, 2010

Related U.S. Application Data

(62) Division of application No. 11/656,350, filed on Jan. 22, 2007, now Pat. No. 7,704,691.

(60) Provisional application No. 60/762,815, filed on Jan. 27, 2006.

(51) Int. Cl.
*C07H 21/04* (2006.01)
*C12Q 1/68* (2006.01)

(52) U.S. Cl. ...... 435/6.1; 435/6.11; 435/6.12; 435/69.1; 536/23.1; 536/24.3

(58) Field of Classification Search .................. None
See application file for complete search history.

(56) References Cited

U.S. PATENT DOCUMENTS 7,704,691 B2 *  4/2010  Braastad et al. ............ 435/6.16
2003/0092019 A1 *  5/2003  Meyer et al. .................... 435/6

FOREIGN PATENT DOCUMENTS
WO   WO 2008/100244 A2   8/2008

OTHER PUBLICATIONS

Pennisi, Science, 1998; 281 (5384):1787-1789.*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Lucentini (The Scientist; 2004, vol. 24, p. 20).*
Moreira et al. Nature Genetics, vol. 36, No. 3, pp. 225-227, Mar. 2004.*
Duquette et al. (Am. Neurological Associations, vol. 57, pp. 408-414, 2005).*
Fogel et al. (Neurology, vol. 67, pp. 2083-2084, Dec. 2006).*

Asaka, T., et al., "Autosomal Recessive Ataxia with Peripheral Neuropathy and Elevated AFP: Novel Mutations in SETX," *Neurology*, 66:1580-1581 (Jan. 2006).
Blair, I.P., et al., "A Gene for Autosomal Dominant Juvenile Amyotrophic Lateral Sclerosis (ALS4) Localizes to a 500-kb Interval on Chromosome 9q34," *Neurogenetics*, 3:1-6 (Jun. 2000).
Bomont, P., et al., "Homozygosity Mapping of Spinocerebellar Ataxia With Cerebellar Atrophy and Peripheral Neuropathy to 9q33-34, and with Hearing Impairment and Optic Atrophy of 6p21-23," *Eur. J. Hum. Gent.*, 8:986-990 (Oct. 2000).
Chance, P.F., et al., "Linkage of the Gene for an Autosomal Dominant Form of Juvenile Amyotrophic Lateral Sclerosis to Chromosome 9q34," *Am. J. Hum. Genet.*, 2:33-40 (Feb. 1998).
Chen, Y.Z., et al., "DNA/RNA Helicase Gene Mutations in a Form of Juvenile Amyotrophic Lateral Sclerosis (ALS4)," *Am. J. Hum. Genet.*, 74:1128-1135 (Apr. 2004).
Chen, Y.Z., et al., "Senataxin, the Yeast Sen1p Orthologue: Characterization of a Unique Protein in Which Recessive Mutations Cause Ataxia and Dominant Mutations Cause Motor Neuron Disease," *Neurobiol. Dis.*, 23:97-108 (Feb. 2006).
Chun, H.H. and R.A. Gatti, "Ataxia-Telagiectasia, an Evolving Phenotype," *DNA Repair*, 3:1187-1196 (May 2004).
Criscuolo, C., et al., "Ataxia With Oculomotor Aprataxia Type 2," *Neurology*, 66:1207-1210 (Jan. 2006).
Duquette, A., et al., "Mutations in Senataxin Responsible for Quebec Cluster of Ataxia with Neuropathy," *Ann. Neurol.* 57:408-414 (Jan. 2005).
Fogel, B.L. and S. Perlman, "Novel Mutations in the Senataxin DNA/RNA Helicase Domain in Ataxia with Oculomotor Apraxia 2," *Neurology*, 67:2083-2084 (Dec. 2006).
Izatt, L., et al., "Autosomal Recessive Spinocerebellar Ataxia and Peripheral Neuropathy with Raised α-Fetoprotein," *J. Neurol.*, 251:805-812 (Jan. 2004).
Le Ber, I., et al., "Cerebellar Ataxia with Oculomotor Apraxia Type 1: Clinical and Genetic Studies," *Brain*, 126:2761-2772 (Sep. 2003).
Le Ber, I., et al., "Frequency and Phenotypic Spectrum of Ataxia with Oculomotor Apraxia 2: A Clinical and Genetic Study in 18 Patients," *Brain*, 127:759-767 (Jan. 2004).
Le Ber, I., et al., "New Autosomal Recessive Cerebellar Ataxias with Oculomotor Apraxia," *Curr. Neurol. Neurosci. Rep.*, 5:411-417 (2005) (month of publ. not avail.).
Mahajnah, M., et al., "Familial Cognitive Impairment with Ataxia with Oculomotor Apraxia," *J. Child Neurol.*, 20:523-525 (Jun. 2005).
Moreira, M.C., et al., "Senataxin, the Ortholog of a Yeast RNA Helicase, is Mutant in Ataxia-Ocular Apraxia 2," *Nature Genetics*, 36:225-227 (Mar. 2004).
Németh, A.H., et al., "Autosomal Recessive Cerebellar Ataxia with Oculomotor Apraxia (Ataxia-Telangiectasia-Like Syndrome) Is Linked to Chromosome 9q34," *Am. J. Hum. Genet.* 67: 1320-1326 (Oct. 2000).
Rabin, B.A., et al., "Autosomal Dominant Juvenile Amyotrophic Lateral Sclerosis," *Brain*, 122:1539-1550 (Mar. 1999).
Nicolaou, P., et al., "A Novel c.5308_5311del1GAGA Mutation in Senataxin in a Cypriot Family with an Autosomal Recessive Cercbcllar Ataxia," *BMC Medical Genetics* research article, vol. 9:28 (2008)(month of publ. not avail.).

(Continued)

*Primary Examiner* — Jeanine A Goldberg
(74) *Attorney, Agent, or Firm* — Hamilton, Brook, Smith & Reynolds, P.C.

(57) ABSTRACT

Methods of identifying polymorphisms associated with ataxia-ocular apraxia 2 (AOA2), are described. The polymorphisms associated with AOA2 include specific mutations in the senataxin (SETX) gene. Also described are methods of diagnosis of AOA2, as well as methods of assessing an individual for carrier status for AOA2.

17 Claims, No Drawings

OTHER PUBLICATIONS

International Search Report from counterpart foreign application PCT/US2007/001570, mailed Nov. 25, 2008.
U.S. Office Action dated Mar. 25, 2008 for U.S. Appl. No. 11/656,350.
U.S. Office Action dated Sep. 11, 2008 for U.S. Appl. No. 11/656,350.
International Search Report for PCT Application No. PCT/US2007/001570, mailed Nov. 25, 2008.

* cited by examiner

METHODS OF DETECTING MUTATIONS ASSOCIATED WITH ATAXIA-OCULAR APRAXIA 2 (AOA2)

RELATED APPLICATION

This application is a divisional of U.S. application Ser. No. 11/656,350, filed Jan. 22, 2007, now U.S. Pat. No. 7,704,691, which claims the benefit of U.S. Provisional Application No. 60/762,815, filed on Jan. 27, 2006. The entire teachings of the above applications are incorporated herein by reference.

BACKGROUND OF THE INVENTION

Ataxia-ocular apraxia 2 (AOA2), or ataxia with oculomotor apraxia type 2, is a recently identified autosomal recessive cerebellar ataxia (Le Ber, I. et al., *Curr. Neurol. Neurosci. Rep.* 2005, 5(5):411-7). Initially associated with a locus at 9q34 (Bomont, P. et al., *Eur. J. Hum. Genet.* 2000, 8:986-990; Nemeth, A. H. et al., *Am. J. Hum. Genet.* 2000, 67:1320-1326; Le Ber, I. et al., *Brain* 2004, 127: 759-767; Izatt, L. et al., *J. Neurol.* 2004, 251:805-812; Mahajnah, M. et al., *J. Child Neurol.* 2005, 20(5):523-525), AOA2 has now been linked to mutations in the senataxin (SETX) gene at that locus (Moreira, M-C. et al., *Nat. Genet.* 2004, 36(3):225-227; Duquette, A. et al., *Ann. Neurol.* 2005, 57:408-414). Certain mutations in the 9q34 locus, including mutations in the SETX gene, have also been associated with an autosomal dominant juvenile amyotrophic lateral sclerosis (ALS4) (Chance, P. F. et al., *Am. J. Hum. Genet.* 1998, 62:633-640; Rabin, B. A. et al., *Brain* 1999, 122:1539-1550; Blair, I. P. et al., *Neurogenetics* 2000, 3:1-6; Chen, Y.-Z. et al., *Am. J. Hum. Genet.* 2004, 74:1128-1135). In addition, AOA2 shares some similarities with other autosomal recessive cerebellar ataxias (ARCAs), including ataxia-telangiectasia (A-T) (Chun, H. H. And R. A. Gatti, *DNA Repair,* 2004, 3:1187-1196) and ataxia with oculomotor apraxia type 1 (AOA1) (Le Ber, I. et al., *Brain* 2003, 126:2761-2772). A need remains for means to distinguish AOA2 from other diseases, and particularly from ALS4 and AOA1.

SUMMARY OF THE INVENTION

The present invention is drawn to methods of assessing an individual for the presence or absence of a genetic polymorphism associated with ataxia-ocular apraxia 2 (AOA2). In the methods of the invention, a test sample from the individual is assessed for the presence of at least one mutation of interest in the senataxin (SETX) gene. Assessing the test sample can be performed by standard methods that may include amplification of all or a fragment of the senataxin gene, and/or direct sequence analysis. The test sample comprises nucleic acids, such as genomic DNA (e.g., genomic DNA comprising chromosome 9 or a fragment thereof comprising 9q34). The mutation of interest is selected from the group consisting of: a single base insertion of T between nucleotides 479-480; a 4 base deletion of nucleotides 4633-4636; a 2 base deletion of nucleotides 6114-6115; a single base transition C→T at nucleotide 6292; a 4 base deletion of nucleotides 369-372; a 2 base insertion of AT between nucleotides 2747-2748; a single base transition C→T at nucleotide 4234; a single base transition C→T at nucleotide 4816; a 6 base deletion of nucleotides 4873-4878 accompanied by an insertion of GG at the same location; a single base insertion of G between nucleotides 4891-4892; a 2 base insertion of CA between nucleotides 5301-5302; a 4 base deletion of nucleotides 5308-5311; a 2 base deletion of nucleotides 5591-5592; a single base deletion of nucleotide 5958; a single base insertion of A between nucleotides 6422-6423; and a four base deletion of nucleotides 6848-6851. The presence of at least one of these mutations of interest is indicative of the presence of a genetic polymorphism associated with ataxia-ocular apraxia 2.

The methods of the invention additionally include methods of diagnosing ataxia-ocular apraxia 2 (AOA2) in an individual, by assessing a test sample from the individual for the presence of at least one mutation of interest, as described above, in a first allele of the senataxin gene of the individual. The presence of a mutation of interest in the first allele of the senataxin gene is indicative of ataxia-ocular apraxia 2 if at least one mutation associated with ataxia-ocular apraxia 2 is also present in the second allele of the senataxin gene. In certain embodiments, both the first and second alleles of the SETX may comprise at least one of the mutations of interest.

The methods of the invention further pertain to methods of assessing an individual for carrier status for ataxia-ocular apraxia 2, by assessing a test sample from the individual for the presence of a mutation of interest, as described above, in first and second alleles of the senataxin gene of the individual. The presence of the mutation of interest in the first allele of the senataxin gene, and the absence of any mutation associated with ataxia-ocular apraxia 2 in the second allele of the senataxin gene, is indicative of carrier status for ataxia-ocular apraxia 2.

The invention further pertains to kits useful in the methods of the invention.

The methods of the invention provide simple means to distinguish ataxia-ocular apraxia 2 from other cerebellar ataxias, as well as to identify those who are affected with the disease or who are carriers for the disease.

DETAILED DESCRIPTION OF THE INVENTION

The present invention provides methods of assessing individuals for the presence or absence of a genetic polymorphism associated with ataxia-ocular apraxia 2 (AOA2), as well as methods of diagnosing AOA2 in an individual, and methods of assessing an individual for carrier status for AOA2. As described herein, Applicant has identified certain mutations of interest in the senataxin gene (SETX gene) that are associated with AOA2. The mutations in the SETX gene described herein are alterations (e.g., deletions, insertions, or transitions) in the nucleic acid sequence of the SETX gene. The position of the mutations in the sequence of SETX are numbered in relation to the mRNA or cDNA sequence: that is, the numbered position of an altered nucleotide is the number of that nucleotide in the mRNA or cDNA sequence. The mRNA sequence associated with the SETX gene is set forth in GenBank accession number AY362728, as updated on Mar. 12, 2004 (also shown in SEQ ID NO:1). The mutations of interest include the following alterations: a single base insertion of T between nucleotides 479-480; a 4 base deletion of nucleotides 4633-4636; a 2 base deletion of nucleotides 6114-6115; a single base transition C→T at nucleotide 6292; a 4 base deletion of nucleotides 369-372; a 2 base insertion of AT between nucleotides 2747-2748; a single base transition C→T at nucleotide 4234; a single base transition C→T at nucleotide 4816; a 6 base deletion of nucleotides 4873-4878 accompanied by an insertion of GG at the same location; a single base insertion of G between nucleotides 4891-4892; a 2 base insertion of CA between nucleotides 5301-5302; a 4 base deletion of nucleotides 5308-5311; a 2 base deletion of nucleotides 5591-5592; a single base deletion of nucleotide 5958; a single base insertion of A between nucleotides 6422-6423; and a four base deletion of nucleotides 6848-6851.

In the methods of the invention, a test sample from an individual is assessed for the presence of one or more of these particular mutations in the SETX gene (herein also referred to as the "polymorphisms of interest" or "polymorphisms associated with AOA2"). The individual is a human individual, and may be of any race and any age, including fetus, infant, juvenile, adolescent, and adult. Representative individuals include those who have not previously been diagnosed as having AOA2 or as being a carrier for AOA2, as well as those who have been determined to be at risk for having AOA2 or for being a carrier for AOA2, and those who have been initially diagnosed as being affected by AOA2, where confirming information is desired.

The test sample is a sample containing nucleic acids comprising the SETX gene or a fragment of the SETX gene, SETX mRNA or a fragment of SETX mRNA, SETX cDNA or a fragment of SETX cDNA, from the individual. The term, "fragment," as used herein, indicates that the portion of the gene, mRNA or cDNA is a polynucleotide of a length that is sufficient to identify it as a fragment of SETX: in a representative embodiment, a fragment comprises one or more exons of the SETX gene; in another representative embodiment, a fragment comprises part of an exon of the SETX gene. The fragment can also include intron/exon junction(s) of the SETX gene.

The test sample is prepared from a biological sample from the individual. The biological sample can be a sample from any source which contains genomic DNA (e.g., chromosomal nucleic acids) or RNA, such as a blood sample, sample of amniotic fluid, sample of cerebrospinal fluid, or tissue sample from skin, muscle, buccal or conjunctival mucosa, placenta, gastrointestinal tract or other organs. A biological sample of nucleic acid from fetal cells or tissue can be obtained by appropriate methods, such as by amniocentesis or chorionic villus sampling (direct or cultured). In certain embodiments, a biological sample containing genomic DNA comprising chromosome 9 or a fragment thereof (e.g., a fragment comprising 9q34, or a fragment comprising one or more exons of the SETX gene) is used. A biological sample can be used as the test sample; alternatively, a biological sample can be processed to enhance access to nucleic acids, or copies of nucleic acids (e.g., copies of nucleic acids comprising the SETX gene), and the processed biological sample can then be used as the test sample. For example, in one embodiment, cDNA is prepared from a biological sample comprising mRNA, for use in the methods. Alternatively or in addition, if desired, an amplification method can be used to amplify nucleic acids comprising all or a fragment of the SETX gene in a biological sample, for use as the test sample in the assessment for the presence or absence of a polymorphism of interest. For example, in a representative embodiment, each of the exons of the SETX gene can be amplified.

The test sample is assessed to determine whether one or more mutations of interest in the SETX gene (polymorphisms of interest) are present in the SETX gene of the individual (e.g., in first and second alleles of the SETX gene). In general, detecting a polymorphism of interest may be carried out by determining the presence or absence of nucleic acids containing the polymorphism of interest in the test sample.

In a first method, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of the polymorphism of interest can be indicated by hybridization of nucleic acid in the genomic DNA, RNA, or cDNA to a nucleic acid probe. A "nucleic acid probe", as used herein, can be a DNA probe or an RNA probe; the nucleic acid probe can contain at least one polymorphism of interest, as described herein. The probe can be, for example, the gene, a gene fragment (e.g., one or more exons), a vector comprising the gene, a probe or primer, etc.

To detect one or more of the polymorphisms of interest, a hybridization sample is formed by contacting the test sample with at least one nucleic acid probe. A preferred probe for detecting mRNA or genomic DNA is a labeled nucleic acid probe capable of hybridizing to mRNA or genomic DNA of the SETX gene. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA or genomic DNA. The hybridization sample is maintained under conditions which are sufficient to allow specific hybridization of the nucleic acid probe to mRNA or genomic DNA of the SETX gene. "Specific hybridization", as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and SETX gene or mRNA in the test sample, the polymorphism that is present in the nucleic acid probe is also present in the SETX gene of the individual. More than one nucleic acid probe can also be used concurrently in this method. Specific hybridization of any one of the nucleic acid probes is indicative of the presence of polymorphism of interest, as described herein.

In Northern analysis (see Current Protocols in Molecular Biology, Ausubel, F. et al., eds., John Wiley & Sons, supra), the hybridization methods described above are used to identify the presence of a polymorphism of interest. For Northern analysis, a test sample comprising RNA is prepared from a biological sample from the individual by appropriate means. Specific hybridization of a nucleic acid probe, as described above, to RNA from the individual is indicative of the presence of a polymorphism of interest, as described herein.

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., *Bioconjugate Chemistry*, 1994, 5, American Chemical Society, p. 1 (1994). The PNA probe can be designed to specifically hybridize to a SETX gene comprising one or more of the polymorphisms of interest described herein. Hybridization of the PNA probe to a SETX gene is indicative of the presence of the polymorphism of interest.

In another method of the invention, mutation analysis by restriction digestion can be used to detect a mutant SETX gene, or an SETX gene containing a polymorphism(s) of interest, if the mutation or polymorphism in the SETX gene results in the creation or elimination of a restriction site. A sample containing genomic DNA from the individual is used. Polymerase chain reaction (PCR) can be used to amplify all or a fragment of the SETX gene (and, if necessary, the flanking sequences) in the sample. RFLP analysis is conducted as described (see Current Protocols in Molecular Biology, supra). The digestion pattern of the relevant DNA fragment indicates the presence or absence of polymorphism in the SETX gene.

Direct sequence analysis can also be used to detect specific polymorphisms of interest in the SETX gene. A sample comprising genomic DNA or RNA is used, and PCR or other appropriate methods can be used to amplify all or a fragment of the SETX gene, and/or its flanking sequences, if desired. The sequence the SETX gene, or a fragment of the gene (e.g., one or more exons), or cDNA, or fragment of the cDNA, or mRNA, or fragment of the mRNA, is determined, using standard methods. The sequence of the gene, gene fragment, cDNA, cDNA fragment, mRNA, or mRNA fragment is compared with the known nucleic acid sequence of the SETX gene, cDNA or mRNA, as appropriate. The presence of a polymorphism of interest can then be identified.

Allele-specific oligonucleotides can also be used to detect the presence of a polymorphism of interest, through the use of dot-blot hybridization of amplified oligonucleotides with allele-specific oligonucleotide (ASO) probes (see, for example, Saiki, R. et al., (1986), Nature (London) 324:163-166). An "allele-specific oligonucleotide" (also referred to herein as an "allele-specific oligonucleotide probe") is an oligonucleotide of approximately 10-50 base pairs, preferably approximately 15-30 base pairs, that specifically hybridizes to the SETX gene, and that contains a polymorphism of interest as described herein. An allele-specific oligonucleotide probe that is specific for particular polymorphisms can be prepared, using standard methods (see Current Protocols in Molecular Biology, supra). To identify polymorphisms of interest, a sample comprising DNA is used. PCR can be used to amplify all or a fragment of the SETX gene, and its flanking sequences. The DNA containing the amplified SETX gene (or fragment of the gene) is dot-blotted, using standard methods (see Current Protocols in Molecular Biology, supra), and the blot is contacted with the oligonucleotide probe. The presence of specific hybridization of the probe to the amplified SETX is then detected. Specific hybridization of an allele-specific oligonucleotide probe to DNA from the individual is indicative of the presence of a polymorphism of interest.

In another embodiment of the invention, fluorescence resonance energy transfer (FRET) can be used to detect the presence of a polymorphism of interest. FRET is the process of a distance-dependent excited state interaction in which the emission of one fluorescent molecule is coupled to the excitation of another. A typical acceptor and donor pair for resonance energy transfer consists of 4-[[4-(dimethylamino) phenyl]azo]benzoic acid (DABCYL) and 5-[(2-aminoethylamino]naphthalene sulfonic acid (EDANS). EDANS is excited by illumination with 336 nm light, and emits a photon with wavelength 490 n×n. If a DABCYL moiety is located within 20 angstroms of the EDANS, this photon will be efficiently absorbed. DABCYL and MANS will be attached to two different oligonucleotide probes designed to hybridize head-to-tail to nucleic acid adjacent to and/or overlapping the site of one of the mutations of interest. Melting curve analysis is then applied: cycles of denaturation, cooling, and re-heating are applied to a test sample mixed with the oligonucleotide probes, and the fluorescence is continuously monitored to detect a decrease in DABCYL fluorescence or an increase in EDANS fluorescence (loss of quenching). While the two probes remain hybridized adjacent to one another, FRET will be very efficient. Physical separation of the oligonucleotide probes results in inefficient FRET, as the two dyes are no longer be in close proximity. The presence or absence of a mutation of interest can be assessed by comparing the fluorescence intensity profile obtained from the test sample, to fluorescence intensity profiles of control samples comprising known mutations of interest in the SETX gene. In another embodiment, arrays of oligonucleotide probes that are complementary to target nucleic acid sequence segments from an individual, can be used to identify polymorphisms of interest. For example, in one embodiment, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, the entire teachings of each of which are incorporated by reference herein. Techniques for the synthesis of these arrays using mechanical synthesis methods are described in, e.g., U.S. Pat. No. 5,384,261, the entire teachings of which are incorporated by reference herein.

Once an oligonucleotide array is prepared, a nucleic acid of interest is hybridized with the array and scanned for polymorphisms. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence which includes one or more previously identified polymorphic markers is amplified by well known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detection of a single polymorphism, arrays can include multiple detection blocks, and thus be capable of analyzing multiple, specific polymorphisms. In alternate arrangements, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional description of use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect polymorphisms of interest. Representative methods include direct manual sequencing (Church and Gilbert, (1988), Proc. Natl. Acad. Sci. USA 81:1991-1995; Sanger, F. et al. (1977) Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V. C. et al. (19891) *Proc. Natl. Acad. Sci. USA* 86:232-236), mobility shift analysis (Orita, M. et al. (1989) *Proc. Natl. Acad. Sci. USA* 86:2766-2770; Rosenbaum and Reissner (1987) *Biophys. Chem.*, 265:1275; Keen et al. (1991) *Trends Genet.*, 7:5; restriction enzyme analysis (Flavell et al. (1978) *Cell* 15:25; Geever, et al. (1981) *Proc. Natl. Acad. Sci. USA* 78:5081); heteroduplex analysis; chemical mismatch cleavage (CMC) (Cotton et al. (1985) *Proc. Natl. Acad. Sci. USA* 85:4397-4401); RNase protection assays (Myers, R. M. et al. (1985) *Science* 230:1242); use of polypeptides which recognize nucleotide mismatches, such as *E. coli* mutS protein (See, for example, U.S. Pat. No. 5,459,039); Luminex xMAP™ technology; and/or allele-specific PCR, for example.

These methods can be used to identify the presence of one or more mutations of interest in the SETX gene as described herein. For example, in certain embodiments, the methods can be used to assess both the first and the second alleles of the SETX gene of an individual for the presence of one or more polymorphisms of interest. The terms, "first" and "second" alleles are arbitrarily applied to the two alleles; that is, either allele may be designated as the "first" allele, and the other allele is then designated as the "second" allele.

In one particular embodiment of the invention, the methods of assessing a test sample for the presence or absence of a mutation in the SETX gene, as described above, are used to assess an individual for the presence or absence of a genetic polymorphism associated with AOA2. The presence of at least one of the mutations of interest (e.g., a single base insertion of T between nucleotides 479-480; a 4 base deletion of nucleotides 4633-4636; a 2 base deletion of nucleotides 6114-6115; a single base transition C→T at nucleotide 6292; a 4 base deletion of nucleotides 369-372; a 2 base insertion of AT between nucleotides 2747-2748; a single base transition C→T at nucleotide 4234; a single base transition C→T at nucleotide 4816; a 6 base deletion of nucleotides 4873-4878 accompanied by an insertion of GG at the same location; a single base insertion of G between nucleotides 4891-4892; a 2 base insertion of CA between nucleotides 5301-5302; a 4 base deletion of nucleotides 5308-5311; a 2 base deletion of nucleotides 5591-5592; a single base deletion of nucleotide 5958; a single base insertion of A between nucleotides 6422-6423; or a four base deletion of nucleotides 6848-6851) is indicative of the presence of a genetic polymorphism associated with AOA2.

In another embodiment of the invention, the methods of assessing a test sample for the presence or absence of a mutation in the SETX gene, as described above, are used to diagnose AOA2 in an individual. Because AOA2 is a recessive cerebellar ataxia, identification of a mutation associated with AOA2 in each allele of the SETX gene of an individual is necessary for diagnosis of AOA2. The two alleles may have the same mutation present, or may have different mutations; furthermore, more than one mutation may be found in one or both alleles. In these methods, at least one polymorphism of interest (a single base insertion of T between nucleotides 479-480; a 4 base deletion of nucleotides 4633-4636; a 2 base deletion of nucleotides 6114-6115; a single base transition C→T at nucleotide 6292; a 4 base deletion of nucleotides 369-372; a 2 base insertion of AT between nucleotides 2747-2748; a single base transition C→T at nucleotide 4234; a single base transition C→T at nucleotide 4816; a 6 base deletion of nucleotides 4873-4878 accompanied by an insertion of GG at the same location; a single base insertion of G between nucleotides 4891-4892; a 2 base insertion of CA between nucleotides 5301-5302; a 4 base deletion of nucleotides 5308-5311; a 2 base deletion of nucleotides 5591-5592; a single base deletion of nucleotide 5958; a single base insertion of A between nucleotides 6422-6423; or a four base deletion of nucleotides 6848-6851) is found in at least one of the two alleles of the SETX gene (the "first" allele). In addition, at least one mutation associated with AOA2 is present in the other allele of the SETX gene (the "second" allele). The mutation associated with AOA2 that is present in the second allele can be a polymorphism of interest as described herein; alternatively, the mutation associated with AOA2 that is present in the second allele can be a mutation in SETX that has been previously associated with AOA2, such as the mutations set forth in Table 1, below.

TABLE 1

Mutations in SETX Previously Associated with AOA2

| Gene Location | cDNA nt Number | nt Change | Codon | aa Change | Outcome | Reference |
|---|---|---|---|---|---|---|
| Exon 3 | 8 | C8T | 3 | T3I | Missense | 2 |
| Exon 4 | 193 | G193A | 65 | E65K | Missense | 3 |
| Exon 8 | 879 | 879delT | 292 | fs after 292 | Frameshift | 1 |
| Exon 8 | 915 | G915T | 305 | W305C | Missense | 1 |
| Exon 8 | 994 | C994T | 332 | R332W | Missense | 1 |
| Exon 10 | 1166 | T1166C | 389 | L389S | Missense | 2 |
| Exon 10 | 1238 | C1238T | 413 | P413L | Missense | 1 |
| Exon 10 | 2332 | C2332T | 788 | R778X | Nonsense | 1 |
| Exon 10 | 2602 | C2602T | 868 | Q868X | Nonsense | 1 |
| Exon 10 | 2622-2625 | 2622-2625delAGTT | 874 | fs after 874 | Frameshift | 1 |
| Exon 10 | 2966-2970 | 2966-2970delGGAAA | 988 | fs after 988 | Frameshift | 1 |
| Exon 10 | 4087 | C4087T | 1363 | R1363X | Nonsense | 1 |
| Exon 10 | 4321 | C4321T | 1441 | Q1441X | Nonsense | 1 |
| Exon 10 | 5070 | 5070insT | 1690 | fs after 1690 | Frameshift | 1 |
| Exon 10 | 5249 | 5249insT | 1750 | fs after 1750 | Frameshift | 1 |
| Exon 10 | 5264 | 5264delC | 1754 | fs after 1754 | Frameshift | 1 |
| Exon 10 | 5267 | T5267C | 1756 | F1756S | Missense | 1 |
| Exon 14 | 5927 | T5927G | 1976 | L1276R | Missense | 3 |

TABLE 1-continued

Mutations in SETX Previously Associated with AOA2

| Gene Location | cDNA nt Number | nt Change | Codon | aa Change | Outcome | Reference |
|---|---|---|---|---|---|---|
| Exon 19 | 6407 | G6407A | 2136 | R2136H | Missense | 2 |
| Exon 20 | 6638 | C6638T | 2213 | P2213L | Missense | 1 |

1 Moreira, M C, et al. Senataxin, the ortholog of a yeast RNA helicase, is mutant in ataxia-ocular apraxia 2. Nature Genetics 2004. March 36(3): 225-7.
2 Chen, Y Z, et al. DNA/RNA helicase gene mutations in a form of Juvenile Amyotrophic Lateral Sclerosis (ALS4). Am. J. Hum. Genet. 2004 (74): 1128-35.
3 Duquette, A, et al. Mutations in Senataxin responsible for Quebec cluster of Ataxia with Neuropathy. Ann. Neurol. 2005. March 57(3): 408-14.

It should be noted that while one or both of the alleles may have a mutation as set forth in Table 1, the methods of the invention require that one or more of the polymorphisms of interest be present in at least one of the alleles, or in both of the alleles, for diagnosis of AOA2 by the methods of the invention.

In a further embodiment of the invention, the methods of assessing a test sample for the presence or absence of a mutation in the SETX gene, as described above, are used to diagnose carrier status of an individual for AOA2. The term, "carrier status," indicates that the individual carries mutation of interest in a single allele of the SETX gene, and no mutations associated with AOA2 in the second allele, and thus is considered a carrier for this recessive cerebellar ataxia. In these methods, at least one polymorphism of interest (a single base insertion of T between nucleotides 479-480; a 4 base deletion of nucleotides 4633-4636; a 2 base deletion of nucleotides 6114-6115; a single base transition C→T at nucleotide 6292; a 4 base deletion of nucleotides 369-372; a 2 base insertion of AT between nucleotides 2747-2748; a single base transition C→T at nucleotide 4234; a single base transition C→T at nucleotide 4816; a 6 base deletion of nucleotides 4873-4878 accompanied by an insertion of GG at the same location; a single base insertion of G between nucleotides 4891-4892; a 2 base insertion of CA between nucleotides 5301-5302; a 4 base deletion of nucleotides 5308-5311; a 2 base deletion of nucleotides 5591-5592; a single base deletion of nucleotide 5958; a single base insertion of A between nucleotides 6422-6423; or a four base deletion of nucleotides 6848-6851) is found in only a first allele of the two alleles of the SETX gene (in the "first" allele). In addition, no mutations associated with AOA2 are found in the second allele of the SETX gene.

It is noted that benign polymorphisms may be present in either or both alleles of the SETX gene.

The present invention also pertains to kits (e.g., reagent kits) useful in the methods of the invention. Such kits comprise components useful in any of the methods described herein, including for example, hybridization probes or primers (e.g., labeled probes or primers), reagents for detection of labeled molecules, restriction enzymes (e.g., for RFLP analysis), allele-specific oligonucleotides, means for amplification of nucleic acids comprising SETX or a fragment of SETX, or means for analyzing the nucleic acid sequence of SETX. For example, in one embodiment, the kit comprises components useful for analysis of mutations of interest using microsphere-based technology such as Luminex xMAP™ technology. In a preferred embodiment of the invention, the kit comprises components for detecting one or more of the mutations of interest (a single base insertion of T between nucleotides 479-480; a 4 base deletion of nucleotides 4633-4636; a 2 base deletion of nucleotides 6114-6115; a single base transition C→T at nucleotide 6292; a 4 base deletion of nucleotides 369-372; a 2 base insertion of AT between nucleotides 2747-2748; a single base transition C→T at nucleotide 4234; a single base transition C→T at nucleotide 4816; a 6 base deletion of nucleotides 4873-4878 accompanied by an insertion of GG at the same location; a single base insertion of G between nucleotides 4891-4892; a 2 base insertion of CA between nucleotides 5301-5302; a 4 base deletion of nucleotides 5308-5311; a 2 base deletion of nucleotides 5591-5592; a single base deletion of nucleotide 5958; a single base insertion of A between nucleotides 6422-6423; or a four base deletion of nucleotides 6848-6851).

The present invention is explained in greater detail in the following non-limiting examples.

Example 1

Identification of Mutations in SETX Gene Associated with AOA2

Patients

Patients assessed for the presence of mutations of interest in the SETX gene included individuals who had previously been diagnosed with ataxia. Characteristics of AOA2 demonstrated by patients generally included one or more of the following: clinical onset between 10 and 22 years of age; severe gait disorder with mildly affected limb and trunk movement; opthalmological symptoms including variably present oculomotor apraxia, disorder smooth pursuit and saccade palsy; peripheral neuropathy including sensory-motor and axonal loss; elevated alpha-fetoprotein (AFP) levels; absent tendon reflexes in legs.

Mutation Screening

Whole blood specimens were obtained from patients, and DNA was extracted using the Puregene Extraction Method (Gentra Systems Inc., Minneapolis, Minn.). Polymerase chain reaction (PCR) was used to amplify genomic DNA; the PCR products were then purified, and cycle sequencing was performed. An ABI Prism® 3730 Genetic Analyzer was used for automated sequencing.

The SETX gene is comprised of 27 exons through 92 kilobases, having an 8,031 base pair coding region that begins within exon 3 and continues to exon 26. To assess for mutations of interest in the SETX gene, all of the SETX coding exons were sequenced. To sequence the SETX coding exons, the gene was broken down into amplicons ranging in size from 311 base pairs to 549 base pairs, in order to allow high quality sequencing of each exon and splice junction with a single primer. Smaller exons (exons 3-9 and 11-25) were amplified using individual exons (including splice junctions) as the amplicons, and exons 10 (4,175 base pairs) and 26 (746 base pairs) were amplified using multiple amplicons. Mutations were verified by sequencing the opposite strand. Primers for amplicons were designed not to overlap with k known deletions or insertions, to minimize the possibility that DNA variants affecting PCR priming sites would result in allele dropout and false normal results. Reference controls included genomic DNA having an identified SETX sequence alteration (positive control), and/or genomic DNA having no SETX alterations (normal controls). Sequences were compared to the SETX mRNA sequence, shown in SEQ ID NO:1.

Results

Several mutations in the SETX gene associated with AOA2 were identified. They are set forth in Table 2, below.

TABLE 2

Mutations of Interest in the SETX Gene, Associated With AOA2

| cDNA nt Number | nt Change | Outcome |
| --- | --- | --- |
| 369-372 | 4 bp Deletion | Frame Shift |
| 2747-2748 | 2 bp Insertion of AT | Frame Shift |
| 4234 | Transition C > T (Homozygous) | Glutamine > Amber (Stop codon) |
| 4816 | Transition C > T | Arginine > OPA (Stop codon) |
| 4873-4878 | 4873-4878del6insGG | Frame Shift |
| 4891-4892 | 1 bp Insertion of G | Frame Shift |
| 5301-5302 | 2 bp Insertion of CA (Homozygous) | Frame Shift |
| 5308-5311 | 4 bp Deletion | Frame Shift |
| 5591-5592 | 2 bp Deletion of AA (Homozygous) | Frame Shift |
| 5958 | 1 bp Deletion of G | Frame Shift |

TABLE 2-continued

Mutations of Interest in the SETX Gene, Associated With AOA2

| cDNA nt Number | nt Change | Outcome |
| --- | --- | --- |
| 6292 | Transition C > T | Arginine > TGA (Stop codon) |
| 6422-6423 | 1 bp Insertion of A (Homozygous) | Frame Shift |
| 6848-6851 | 4 bp Deletion | Frame Shift |
| 479-480 | 1 bp insertion of T | Frame Shift |
| 4633-4636 | 4 bp deletion of AGTG (Homozygous) | Frame Shift |
| 6114-6115 | 2 bp Deletion of TG | Frame Shift |

Of these mutations, five were homozygous; the presence of the homozygous mutation, in combination with AOA2 symptoms, indicated that these mutations were associated with the presence of AOA2. The remainder of the mutations were heterozygous, and were associated with AOA2 because the individuals having those mutations in one allele were symptomatic for AOA2 and also had a second mutation associated with AOA2 present in the second allele.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of assessing a human individual for the presence of a genetic polymorphism associated with ataxia-ocular apraxia 2 (AOA2), the method comprising (a) assessing a test sample from the individual for the presence of at least one mutation of interest in the senataxin (SETX) gene, wherein the mutation of interest is a 4 base deletion of nucleotides 4633-4636, and (b) detecting the presence of the 4 base deletion of nucleotides 4633-4636, wherein the nucleotide numbering is as shown in SEQ ID NO:1, and
   wherein the presence of the mutation of interest is indicative of the presence of a genetic polymorphism associated with ataxia-ocular apraxia 2.

2. The method of claim 1, wherein the test sample from the individual comprises genomic DNA.

3. The method of claim 2, wherein the genomic DNA comprises chromosome 9 or a fragment thereof comprising 9q34.

4. The method of claim 1, wherein assessing the test sample comprises amplifying all or a fragment of the senataxin gene.

5. The method of claim 1, wherein assessing the test sample comprises direct sequence analysis.

6. A method of diagnosing ataxia-ocular apraxia 2 (AOA2) in a human individual with ataxia, comprising (a) assessing a test sample from the individual for the presence of at least one mutation of interest in a first allele of the senataxin (SETX) gene of the individual, wherein the mutation of interest is a 4 base deletion of nucleotides 4633-4636 in a first allele of the senataxin (SETX) gene, wherein the nucleotide numbering is as shown in SEQ ID NO:1, and (b) diagnosing the individual as having AOA2 when said 4 base deletion of nucleotides 4633-4636 is detected in the first allele of the senataxin gene, and any mutation associated with ataxia-ocular apraxia 2 is present in a second allele of the senataxin gene.

7. The method of claim 6, wherein the second allele of the senataxin (SETX) gene comprises at least one mutation of interest selected from the group consisting of:
   a) a 4 base deletion of nucleotides 369-372;
   b) a 2 base insertion of AT between nucleotides 2747-2748;
   c) a single base transition C→T at nucleotide 4234;
   d) a single base transition C→T at nucleotide 4816;
   e) a 6 base deletion of nucleotides 4873-4878 accompanied by an insertion of GG at the same location;
   f) a single base insertion of G between nucleotides 4891-4892;
   g) a 2 base insertion of CA between nucleotides 5301-5302;
   h) a 4 base deletion of nucleotides 5308-5311;
   i) a 2 base deletion of nucleotides 5591-5592;
   j) a single base deletion of nucleotide 5958;
   k) a single base insertion of A between nucleotides 6422-6423;
   l) a single base transition C→T at nucleotide 6292;
   m) a four base deletion of nucleotides 6848-6851;
   n) a single base insertion of T between nucleotides 479-480;
   o) a 4 base deletion of nucleotides 4633-4636; and
   p) a 2 base deletion of nucleotides 6114-6115.

8. The method of claim 7, wherein both the first and the second alleles of the senataxin gene comprise a 4 base deletion of nucleotides 4633-4636.

9. The method of claim 6, wherein the test sample from the individual comprises genomic DNA.

10. The method of claim 9, wherein the genomic DNA comprises chromosome 9 or a fragment thereof comprising 9q34.

11. The method of claim 6, wherein assessing the test sample comprises amplifying all or a fragment of the senataxin gene.

12. The method of claim 6, wherein assessing the test sample comprises direct sequence analysis.

13. A method of assessing a human individual for carrier status for ataxia-ocular apraxia 2 (AOA2), the method comprising (a) assessing a test sample from the individual for the presence of a mutation of interest in the senataxin (SETX) gene of the individual, wherein the mutation of interest is a 4 base deletion of nucleotides 4633-4636, and (b) detecting the presence of the 4 base deletion of nucleotides 4633-4636 in a first allele of the senataxin (SETX) gene, wherein the nucleotide numbering is as shown in SEQ ID NO:1, and wherein the presence of the mutation of interest in the first allele of the senataxin gene, and the absence of any mutation associated with ataxia-ocular apraxia 2 in a second allele of the senataxin gene, is indicative of carrier status for ataxia-ocular apraxia 2.

14. The method of claim 13, wherein the test sample from the individual comprises genomic DNA.

15. The method of claim 14, wherein the genomic DNA comprises chromosome 9 or a fragment thereof comprising 9q34.

16. The method of claim 13, wherein assessing the test sample comprises amplifying all or a fragment of the senataxin gene.

17. The method of claim 13, wherein assessing the test sample comprises direct sequence analysis.

* * * * *

SEQUENCE LISTING

<160> NUMBER OF SEQ ID NOS: 1

<210> SEQ ID NO 1
<211> LENGTH: 8034
<212> TYPE: DNA
<213> ORGANISM: Homo Sapiens

<400> SEQUENCE: 1

```
atgagcacat gttgttggtg tacgccaggt ggtgcttcca ccattgactt cctaaagcgc      60
tatgcttcca acactccgtc cggtgaattt caaacagccg acgaagacct ctgctactgc     120
ttggagtgtg tggctgagta ccacaaagca agagatgaat tgccattctt gcatgaggtt     180
ttatgggaat tagaaacctt acgtctcata aatcactttg aaaaatccat gaaggcagaa     240
attggagatg atgatgagtt atatatagta gacaataatg gagagatgcc actgtttgac     300
atcactgggc aagactttga aaataagctt cgagttcctc ttcttgaaat actgaaatat     360
ccttacttgc ttctacatga acgtgttaac gagttatgtg ttgaagcact tgtcggatg      420 gaacaagcca attgctcctt tcaggtgttt gataaacatc cagggatcta tttgttttta     480
gtccatccca atgaaatggt tcggcgttgg gctatcttga ctgcaagaaa cttggggaaa     540
gtggacagag atgattatta tgacttacaa gaagttttac tttgcctttt taaagtcatt     600
gagttggggc ttttagagag tccagacatt tatacttctt ctgtcctaga gaagggtaaa     660
ctgattcttc tgccctcaca catgtatgat actaccaact acaaaagcta ttggttaggt     720
atttgcatgt tgctgaccat tcttgaggaa caagccatgg attccctgtt gttgggctca     780
gacaaacaaa atgattttat gcaatcgata cttcacacta tggagaggga agcagatgat     840
gatagtgtgg atcctttctg gccagcgtta cactgtttta tggtgattct ggatcgcctt     900
ggatctaagg tctggggtca acttatggat cctattgtgg catttcaaac cattatcaac     960
aacgcaagct acaatagaga gatccgacat atacggaaca gctctgtaag gaccaagtta    1020
```

| | |
|---|---|
| gaaccggagt cctatttgga tgatatggtg acttgcagcc agatcgtata caattataat | 1080 |
| cctgaaaaga ccaaaaagga ttctggatgg agaacagcca tttgcccaga ttattgtcct | 1140 |
| aacatgtatg aagaaatgga acattagcc agtgtacttc agtcagatat tggtcaagac | 1200 |
| atgcgtgttc ataacagcac atttctatgg ttcatcctt ttgtccagtc cctcatggat | 1260 |
| cttaaggatt tgggtgtggc ttacatagca caggttgtta atcatctgta ctctgaagtc | 1320 |
| aaagaagtcc tcaaccaaac agatgctgtg tgtgacaaag tcactgaatt ttttcttcta | 1380 |
| attttggtat cagtgattga actgcataga aataaaaaat gttttgcattt gctgtgggta | 1440 |
| agttcccagc aatgggtgga agccgtcgtc aaatgtgcca agcttcctac cactgcgttt | 1500 |
| acacggagtt ctgagaaatc atctggaaat tgctccaaag gaacagcaat gatatcttca | 1560 |
| ctgtcattgc attccatgcc atctaactct gtacaacttg cttatgtgca gctgattaga | 1620 |
| agtctcctta aagaaggtta tcagcttggg cagcagtctc tttgcaagcg attctgggat | 1680 |
| aagctcaact tattccttag aggaaattta tctctaggtt ggcagttgac tagtcaggaa | 1740 |
| acccatgagc tacaaagttg cttaaagcaa attattagaa acataaaatt caaagcacct | 1800 |
| ccatgtaaca cttttgtgga tctgacttct gcatgtaaaa tctctcctgc atcttataat | 1860 |
| aaagaagaaa gtgaacaaat ggggaagacg tctagaaaag atatgcattg tttggaagct | 1920 |
| tccagcccaa cattttctaa agaaccaatg aaagtgcaag acagtgtatt gatcaaagca | 1980 |
| gataacacta tagaaggtga caataatgag caaaattata taaggatgt gaaactagag | 2040 |
| gaccatctct tagctgggtc atgcttaaag cagagtagta aaaacatttt tactgaaaga | 2100 |
| gctgaagatc aaattaaaat aagtacaagg aagcagaagt ctgtaaaaga gatctcttca | 2160 |
| tatacaccaa aggactgtac ttcaagaaat ggtccagaaa ggggatgtga cagaggaata | 2220 |
| atagtatcaa cacgtttgtt gactgattct agcactgatg ctttggaaaa agtgtccaca | 2280 |
| tcgaatgaag atttctcttt aaaggatgat gctcttgcta aaacctcaaa acgaaaaact | 2340 |
| aaggtacaga aagatgaaat ctgtgcaaag ttatcacatg taataaagaa gcaacacagg | 2400 |
| aagagtactt tggtcgataa tactatcaat ttagatgaaa atttgactgt atctaacatt | 2460 |
| gagagtttct attcaaggaa agatacagga gttcagaaag gagatggttt catacacaat | 2520 |
| ctttctttag accctagtgg tgttctggat gataagaatg gagaacaaaa atctcaaaac | 2580 |
| aatgtattgc caaaagagaa acaattaaag aatgaagaat tagttatttt ctcttttccat | 2640 |
| gaaaacaatt gtaaaataca ggaatttcat gttgatggta agaattgat ccctttaca | 2700 |
| gaaatgacca atgcttcaga gaagaaatca tctccctta aagatcttat gactgtacct | 2760 |
| gaatcaagag atgaggagat gagtaatagt accagtgtga tttattctaa cttgacaaga | 2820 |
| gaacaggccc ctgacatcag tcctaaatct gacaccttaa cggattctca gatagacaga | 2880 |
| gaccttcaca aattatcttt actagctcaa gccagtgtta ttacgttccc atccgattca | 2940 |
| cctcagaact catcgcagct gcaaaggaaa gtaaagaag ataaagatg tttcacagct | 3000 |
| aaccaaaata atgttggaga tacctcccgt ggacaggtta ttattattc agattctgat | 3060 |
| gatgatgatg atgaaagaat cctgagtctt gagaaactca ctaaacagga caaaatatgc | 3120 |
| cttgagaggg aacatccaga gcagcacgtt tcaacagtta atagtaagga ggaaaagaat | 3180 |
| ccagtaaagg aagaaaagac agagactctt tttcagtttg aggaatctga ttctcagtgt | 3240 |
| tttgagtttg aaagttcatc tgaagtgttt tcagtttggc aagatcatcc agacgataat | 3300 |
| aattcagttc aagatggtga gaaaaatgt ttggctccta tagccaatac tacaaatggt | 3360 |
| cagggttgta cagattatgt atctgaagtt gttaaaaaag gagcagaggg cattgaagaa | 3420 |

```
cacacaagac cacggagtat ttctgttgaa gaatgttgtg aaattgaagt aaaaaagcct    3480
aagagaaaac gatctgaaaa accaatggct gaagatcctg tgaggccttc atcttctgtc    3540
agaaatgagg gccagtctga tactaataag agagatcttg tgggaaatga ttttaaaagt    3600
attgatagaa ggacttcaac tcccaattca cgtattcaga gagccactac ggtttcacaa    3660
aagaagtctt caaagctttg tacttgtaca gaacccatca ggaaagttcc agtttctaag    3720 accccctaaga aaactcattc agatgccaaa aaggacaga atagaagttc aaattaccta    3780
agttgtagaa caactcctgc tatagtgccg ccaaagaaat ttcgtcagtg tcctgagcca    3840
acttcaacag ctgagaaact tggcctgaaa aagggtcctc gtaaggcata tgagttgtcc    3900
cagcggtctt tggattatgt agctcaatta cgtgatcatg gcaaaactgt tggagtagtt    3960
gatacccgaa aaaagactaa attaatttct cctcagaacc tgtctgtcag aaataataag    4020
aaacttctga ctagtcaaga acttcagatg caaaggcaga tcagacccaa atcacaaaaa    4080
aatagacgaa gactttctga ttgtgaaagt acagatgtta aaagagcagg gtcacataca    4140
gcacagaatt ctgacatatt tgtaccagaa tctgataggt cagattataa ttgtacagga    4200
ggaactgagg tacttgccaa cagtaacaga aaacagttaa taaaatgcat gccttctgaa    4260
ccagaaacca taaaagcaaa acatgggtct ccagcaactg atgatgcttg ccctttgaac    4320
cagtgtgatt ctgtagtgtt aaatggaaca gtaccaacaa atgaagtaat tgtctccact    4380
tcagaagacc ctctgggtgg aggtgatcca acagcacgtc atatagagat ggcagctttg    4440
aaagaaggag agcctgactc cagcagtgat gcagaggaag ataacttatt tttaacccaa    4500
aatgatcctg aagatatgga tttatgttca caaatggaga atgacaatta taaactcatt    4560
gaactaattc atggaaaaga tacagttgag gttgaagaag attctgtaag tcggcctcag    4620
ttggaatctt tgagtggcac aaagtgtaag tacaaagatt gtcttgaaac cacaaaaaac    4680
cagggtgaat actgcccaaa acactctgaa gtgaaagcag cagatgaaga tgtatttcgt    4740
aaacctggct tgcctcctcc tgcatctaaa cctttgagac ctaccactaa gattttagc    4800 tcaaagagta cttcacgaat tgctggtctt tctaaatctt tggaaacttc ttcagcactt    4860
tcaccgtctc taaaaaataa gtcaaagggg atacagtcga ttttgaaagt accacagcca    4920
gttcccctca tagctcagaa gccagttggt gaaatgaaga attcgtgcaa tgttcttcat    4980
cctcagtctc cgaataattc caacaggcaa ggttgcaaag ttccatttgg tgaaagcaaa    5040
tattttccat cttcctctcc agtaaacatt cttttgtcat cacagtctgt ctctgacacc    5100
ttcgttaaag aggtcttaaa atggaaatat gaaatgtttt tgaactttgg tcagtgtggg    5160
ccccctgcaa gtctttgtca gtccatctca agacctgtgc ctgtcagatt tcacaattat    5220
ggagattatt ttaatgtttt tttccctttg atggtattga atactttga aacagtggca    5280 caagaatggc tcaactctcc aaatagagag aatttctatc agttgcaagt acgaaaattt    5340
cctgccgatt atataaaata ctgggagttt gcagtttatc tggaagaatg tgaactggct    5400
aaacagcttt atccaaagga aaacgatttg gtgttttag ctcctgagag aataaatgaa    5460
gagaagaaag atacagagag aaatgacata caagatctcc acgaatatca ttctggttat    5520
gttcataaat ttcgccgcac gtcagtcatg cgtaatggga aaactgagtg ttaccttccc    5580
atccagactc aagagaacct tccggccaat ttaaacgaac ttgtgaattg tattgtaatc    5640
agttctctgg taactacaca aaggaagttg aaagccatgt ctctgttggg tagtcggaac    5700
caactggcta gagctgttct gaatccaaac cctatggact tctgtacaaa agatttactg    5760
actacaacat ctgagagaat tattgcgtac ttaagagatt tcaatgaaga tcaaaagaaa    5820
```

```
gcaatagaaa ctgcatatgc tatggtgaaa cactcaccat cagttgccaa aatctgcttg   5880
attcatggac cacctggaac aggaaaatca aaaactattg ttggcctcct ctatcgtcta   5940
ctgacagaga accagaggaa ggggcattca gacgaaaact ccaatgccaa aatcaaacaa   6000
aaccgtgtcc tcgtgtgtgc accttccaat gcagctgttg atgaactcat gaaaaaaatt   6060
atccttgaat tcaaagaaaa atgtaaagac aagaagaatc ctttaggaaa ctgtggagat   6120
ataaatttag tacgactggg tccagaaaag tctattaata gtgaggttct aaagttcagt   6180
ttggacagcc aagtaaacca cagaatgaaa aaagagttac cttctcatgt tcaggcgatg   6240 cataaagaa aggaatttct agattatcag ctggatgagc tttcccggca gcgagctcta   6300
tgccgaggtg gacgggaaat acagaggcaa gaattagatg aaaacatttc caaagtttct   6360
aaggaaaggc aggaacttgc ttctaaaatt aaagaggttc aaggacgccc acagaaaaca   6420
cagagtatca tcatcttaga gtcccatatc atctgctgca cgttgagcac aagtggtggt   6480
ttactacttg agtctgcttt ccgtgggcaa ggggtgtcc ccttcagctg tgtcattgtt   6540
gatgaggctg gacagtcttg tgaaattgag actcttactc cactcatcca tcgctgcaat   6600
aagctcatcc tagtaggaga tcctaagcag ctccctccga cagtcatctc tatgaaagca   6660
caggagtatg gctacgacca gtcaatgatg gctcgcttct gcagactgct ggaagagaat   6720
gtagaacaca acatgatcag caggctgccc attctacagc tcactgttca gtacaggatg   6780
catccagaca tatgcctctt cccttctaat tatgtttata acagaaactt aaaaacaaat   6840
agacagacag aagccattcg atgttcatca gattggccat ttcagccata ccttgtgttt   6900
gatgttggag atggttcaga aagacgggat aatgactcat atataaatgt tcaagaaata   6960
aaactggtga tggaaataat taagcttatt aaagacaaaa gaaggatgt tagttttcga   7020 aacattggca taataactca ttacaaggcc cagaagacga tgattcagaa ggatttggac   7080
aaagagttcg atagaaaagg accagcagaa gtagacactg tggatgcatt ccagggtcgg   7140
cagaaggatt gtgttattgt tacgtgtgtc agagcaaata gcatccaagg ttcaattgga   7200
ttcctggcaa gtttgcagag attgaatgtc accatcacac gagccaagta cagcctcttc   7260
atcctcggac atttgaggac cctgatggaa aaccagcatt ggaatcagct gattcaggat   7320
gctcagaagc gtggtgccat tattaagacc tgtgacaaaa actatagaca tgatgcagtg   7380
aagattctga aactcaagcc tgtgctgcag agaagtctca ctcaccctcc taccatagcc   7440 ccagagggt ccagaccca gggtggtttg cccagcagca agctagacag tggatttgcc   7500
aagacatctg ttgctgcttc tctataccac acaccctctg actccaagga aattactctt   7560
actgttactt caaggaccc tgaaagacct cctgttcatg accaacttca ggacccacga   7620
ctgctgaaga ggatgggcat tgaggtcaaa ggaggaatat cctttggga tccacaaccc   7680 tcgagccccc agcatcctgg agcaacacct cctacgggcg agccgggctt ccctgtcgtt   7740
caccaggacc tgagccatat acagcagccc gctgctgtag tggctgctct gagcagccac   7800
aaacctcccg tgcggggcga acctccagct gccagtcccg aggcttccac gtgtcagagc   7860
aaatgtgatg acccggaaga ggagctctgt cacaggagag aggccagggc tttcagtgaa   7920
ggggagcagg agagtgtgg ttccgagacc catcacacca ggaggaactc taggtgggac   7980
aagaggacac tggagcagga ggacagcagt tccaagaaaa gaaagctttt atag         8034
```